United States Patent [19]

Tomioka et al.

[11] Patent Number: 5,219,738

[45] Date of Patent: Jun. 15, 1993

[54] ANIMAL CELL TRANSFORMANT, METHOD FOR OBTAINING THE TRANSFORMANT AND METHOD FOR PRODUCING DESIRED FOREIGN GENE PRODUCT BY USING THE TRANSFORMANT

[75] Inventors: Noboru Tomioka, Mobara; Fumio Omae, Yokohama; Eriko Mine, Taito; Tomoko Ishii, Chosei, all of Japan

[73] Assignee: Mitsui Toatsu Chemicals, Incorporated, Japan

[21] Appl. No.: 45,512

[22] Filed: May 4, 1987

[30] Foreign Application Priority Data

May 10, 1986 [JP] Japan .................. 61-105824

[51] Int. Cl.$^5$ ............... C12P 21/02; C12N 15/00; C12N 5/00; C12N 7/00
[52] U.S. Cl. ................. 435/69.1; 435/91; 435/172.3; 435/240.2; 435/320.1; 435/235.1; 536/23.2; 530/350; 935/9; 935/32; 935/34; 935/42; 935/57; 935/61; 935/70
[58] Field of Search ............ 435/68, 70, 91, 172.1, 435/172.3, 240.2, 320, 69.1, 69.6; 530/350;. 536/27; 935/6, 9, 19, 23, 42, 70

[56] References Cited

U.S. PATENT DOCUMENTS

| | | | |
|---|---|---|---|
| 4,399,216 | 8/1983 | Axel et al. | 435/6 |
| 4,965,199 | 10/1990 | Capon et al. | 435/69.6 |

FOREIGN PATENT DOCUMENTS

| | | | |
|---|---|---|---|
| 23531/84 | 7/1984 | Australia . | |
| 23533/84 | 7/1984 | Australia . | |
| 23534/84 | 7/1984 | Australia . | |
| 0093619 | 11/1983 | European Pat. Off. . | |
| 0117059 | 1/1984 | European Pat. Off. . | |
| 0117058 | 8/1984 | European Pat. Off. . | |
| 0117060 | 8/1984 | European Pat. Off. | 435/172.1 |
| 0159714 | 4/1985 | European Pat. Off. . | |
| 0223230 | 2/1987 | European Pat. Off. . | |
| 8605807 | 10/1986 | PCT Int'l Appl. . | |

OTHER PUBLICATIONS

Nat Acad Science USA Ny et al 81, 5355-5359 "Structure of the human tissue-type plasminogen activator gene . . . domains" (1984).

Lee et al Nature vol. 294 Nov. 1981 228-232 (1981) "Glucocorticoids regulate expression . . . chimaeric plasmids".

Schimke (1981) Gene Amplification CSH Lab 1-6 "Studies on Gene Duplications and Amplifications . . . Perspective".

Ringold et al (1981), J. Mol Appl Genetics 1 165-175 "Co-Expression and Amplification of . . . Ovary Cells".

Kaufman et al (1985) Mol and Cell Biol 5 1750-1759 "Coamplification and Coexpression of Human . . . Ovary Cells".

Simonson et al Proc. Natl Acad Sci USA 80, 2495-2499 "Isolation and expression of an altered mouse dihydrofolate . . . cDNA".

Deschatrette et al Proc Natl Acad Sci USA 82, 765-769 "Expression of the mouse serum . . . hepatoma cells".

Breathnach (1984), The EMBO Journal vol. 3, No. 4, 901-908 "Selective amplification in methotrexate-resistant . . . sites".

Scahill et al Proc. Natl. Acad Sci USA vol. 80, 4564-4658 (1983) "Expression and characterization of the . . . ovary cells".

Crowley et al Molecular and Cellular Biology (1983) 44-55 "Plasmid-Directed Synthesis of Hepatitis . . . Monkey Cells".

Schimke, R. T., et al Cold Spray Holder Symp. Quant. Biol. vol. 45 pp. 785-797 (1981).

Murray et al Mol. Cell. Bio vol. 3 pp. 32-43 (1983).

"Transformation of Mammalian Cells With an Amplifiable Dominant-Acting Gene" *Proceedings of the National Academy of Sciences of the USA*, Jun. 1980, pp. 3567-3570, vol. 77, No. 6, Wigler et al.

*Primary Examiner*—Joan Ellis
*Attorney, Agent, or Firm*—Nixon & Vanderhye

[57] ABSTRACT

By screening an animal cell transformant, which has been obtained by introducing into wild-type animal cells a wild-type DHFR gene and a structural gene which codes a desired useful substance, with a medium containing methotrexate (MTX) at a concentration of 50 μM or lower, both genes can be amplified effectively within an MTX resistant strain and a stable amplified transformant can also be obtained. The screening may be repeated using an increasing concentration of MTX. It is also possible to obtain stably the desired foreign gene product in a high yield by using the thus-obtained amplified transformant.

20 Claims, 1 Drawing Sheet

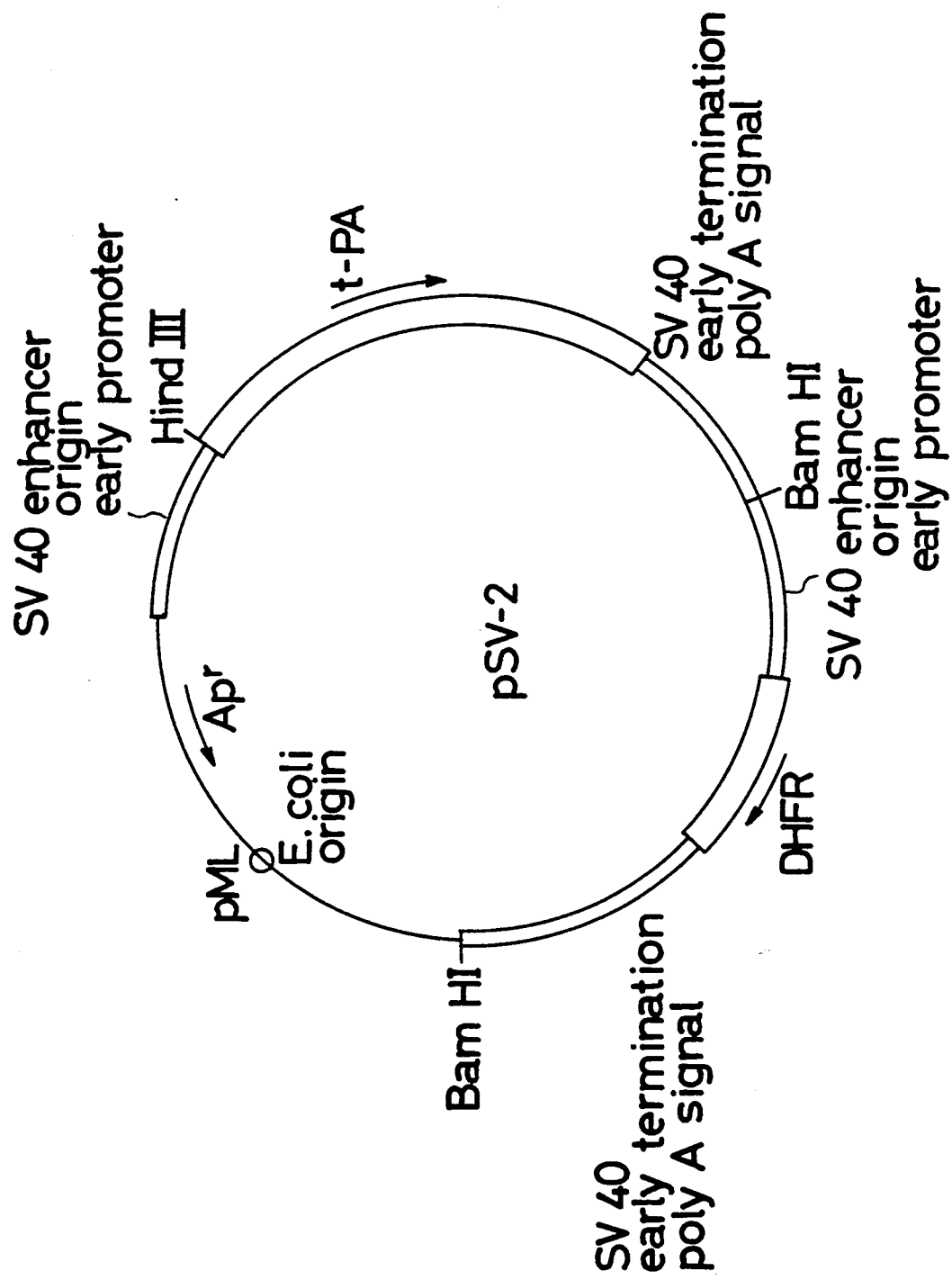

ANIMAL CELL TRANSFORMANT, METHOD FOR OBTAINING THE TRANSFORMANT AND METHOD FOR PRODUCING DESIRED FOREIGN GENE PRODUCT BY USING THE TRANSFORMANT

BACKGROUND OF THE INVENTION

1) Field of the Invention

This invention relates to a technique for introducing a wild-type DHFR gene, which codes for dihydrofolate reductase, as a dominant selective marker into wild-type animal cells to obtain a transformant and then culturing the transformant in an amplification medium containing a DHFR inhibitor to obtain an amplified transformant having amplified productivity of a useful substance. This invention can be used effectively as a technique for the production of tissue plasminogen activator (hereinafter abbreviated as "t-PA").

An object of this invention is to obtain an amplified transformant from a transformant, which itself contains a desired gene, by a specific method. It is another feature of this invention that the amplified transformant contains a foreign wild-type DHFR gene.

2. Description of the Prior Art

A DHFR gene codes for dihydrofolate reductase, which takes part in the biosynthesis of DNA and RNA, and the gene can be amplified within cells resistant to methotrexate (MTX) which is known as a carcinostatic agent.

Attempts have been made to amplify a desired foreign gene within a transformant by use of DHFR gene amplification so that the production level of a foreign gene product could be improved.

Co-amplification of the DHFR gene and the desired foreign gene is performed by culturing a transformant, which contains the DHFR gene and the foreign gene, in a fresh medium with a higher concentration of MTX and screening a strain resistant to the higher MTX concentration by using the DHFR gene as a marker. This operation may be repeated in a much higher concentration of MTX.

As useful DHFR gene sources, there are both wild-type and mutant-type. When a wild-type DHFR gene is chosen, a DHFR-deficient strain is generally used as a host.

As one example of the application of a mutant DHFR gene, European Patent Publication No. 117059-A discloses a technique for obtaining t-PA producing transformants by using a mutant DHFR gene as a dominant selective marker gene for wild-type cells to give MTX (methotrexate) resistance to the cells, selecting the transformant which was co-transfected with a human t-PA gene and then culturing the thus-obtained transformant in the presence of MTX at higher concentration so as to increase both of the DHFR and t-PA genes.

The above conventional technique is however accompanied by problems. Firstly, the mutant DHFR gene yields due to its mutation a genetic product in which the 22th amino acid has been changed from leucine to arginine. Possible adverse effects such as malignant growth which such a mutant DHFR gene or its genetic product may cause on the wild-type cells employed as a host, have not been fully investigated. As a pharmaceutical technique which is supposed to meet stringent safety requirements, the use of the mutant DHFR gene is still considered to involve unsolved problems.

The mutant DHFR gene is different in its binding affinity to MTX from wild-type DHFR genes and the binding affinity of the former gene is as weak as one two hundred seventieth of the binding affinity of the latter.

In a series of gene multiplication operations for obtaining an MTX-resistant strain in the presence of MTX at an increased concentration, it is accordingly indispensable to culture transformed cells with the mutant DHFR gene at a considerably higher MTX concentration when compared to the case of using wild-type DHFR genes.

The MTX concentration required for the culture of the amplified transformants is much higher than that employed when wild-type DHFR genes are used. Since such a high MTX concentration is harmful to cells, a resistant strain obtained in the presence of MTX at such a high concentration is itself unstable. Under the current technology, the above described selection method in which a high MTX concentration was employed to obtain amplified transformants has not yet resulted in any reproducible and practical technique.

For the reasons mentioned above, the method for forming a high t-PA producing transformant by use of a mutant DHFR gene is still believed to be incomplete as a technique to be used for the production of pharmaceutical products.

Wild-type cells capable of expressing their DHFR gene are usually chosen as host animal cells, because mutant cells are not easily established in the case of animal cells and therefore the mutant cells are not advantageous for industrial production. However, a transformant may not always be obtained stably when a wild-type DHFR gene is used as a dominant selective marker gene for such wild-type cells. Even if a transformant could be obtained, the expression of the characters by the transformant is unexceptionally unstable. Difficulties are therefore encountered in many instances upon screening a transformant by this method. As a matter of fact, no stable t-PA producing strain was obtained when a wild-type DHFR gene was used for wild-type Chinese hamster cells (European Patent Publication No. 117060-A).

It may therefore be contemplated that a wild-type DHFR gene could be used as a selective marker gene if a DHFR-deficient strain can be established from wild-type cells. This approach is however not easy, because the establishment of such a DHFR-deficient strain per se is complex and time-consuming. [For details, reference may be had to Urlanb, G., & Chasin, L. A., Proc. Natl. Acad. Sci. U.S.A., 77, 4216 (1980).]

SUMMARY OF THE INVENTION

The present inventors found that the drawbacks from the use of a mutant DHFR gene can be overcome and that an extremely advantageous method, which can realize a stable production of a useful foreign gene product such as human t-PA with good reproducibility, can be provided, when a wild-type DHFR gene can be introduced as a dominant selective marker for wild-type animal cells which are suitable for industrial production. A further extensive investigation has then been carried out on the method.

From the fact that wild-type animal cells can no longer survive when the endogenous DHFR is inactivated in the presence of MTX at an effective concentration, it is readily expected on the basis of the prior art that when an exogenous wild-type DHFR gene was introduced into the wild-type cells, the exogenous DHFR gene would be inactivated like the endogenous DHFR in the presence of MTX at the effective concentration and no stable transformant would hence be obtained.

In spite of such a prediction, the present inventors selected animal cells, which are advantageous for industrial production, as host cells and have studied various conditions and various combinations of animal cells and wild-type DHFR genes to obtain stable MTX resistant transformants. As a result, the present inventors have unexpectedly succeeded in obtaining a stable transformant in the present of MTX at the effective concentration, leading to completion of the present invention.

An object of this invention is therefore to solve the above-described various problems of the prior art and to obtain a higher transformant having stable and high productivity of a useful substance.

Another object of this invention is to provide a method for producing a useful substance efficiently by using a transformant which retains stable and high productivity of the useful substance.

These objects can be achieved by a method for obtaining an amplified transformant, which comprises introducing a wild-type DHFR gene and a structural gene, which codes the useful substance, in animal cells to obtain a transformant of the animal cells and then culturing the transformant in an amplification medium containing methotrexate (MTX) at a concentration of 50 $\mu$M or lower so as to amplify both genes, and by the transformant obtained in accordance with the above method.

According to the present invention, drug resistance is introduced into industrially-useful wild-type animal cells, thereby making it possible to screen cells transformed simultaneously by a vector containing a desired foreign gene such as the human t-PA gene. Further, an amplified transformant is also obtained to permit the production of a useful substance stably in a high yield.

When the present invention is employed, the amplification of the genes is conducted on a transformant in the presence of MTX at a concentration lower than that employed in the prior art (for example, at 0.25 $\mu$M). It is therefore possible to obtain a transformant having stable and high productivity of a useful substance.

BRIEF DESCRIPTION OF THE DRAWING

FIG. 1 shows the structure of plasmid pSV-2 to be expressed, which was used in Example of this invention.

DETAILED DESCRIPTION OF THE PREFERRED EMBODIMENTS

In the method of this invention, either separate vectors or the same vector containing a desired foreign gene and a wild-type DHFR gene is introduced into wild-type animal cells. In a selective medium containing MTX at an effective concentration, transformants are screened. Transformants that express the desired foreign gene are screened from the MTX resistant transformants. With respect to the thus-obtained transformant, an amplifying operation for the selective marker gene is conducted in the presence of an increased concentration of MTX at a concentration of 50 $\mu$M or lower so as to obtain a transformant which expresses the desired foreign gene with high productivity. In addition, the product of the desired foreign gene is also co-amplified by the operation.

As the desired foreign gene to be amplified, any one of various genes corresponding to target products can be used.

For example, t-PA is an enzyme included in a fibrinolytic system. Since the lysis of fibrin clots, thrombus constituents, begins upon activation by t-PA, t-PA is useful as a novel therapeutic drug for thrombosis. In the production of human t-PA, it is possible to use as a human t-PA gene that available as cDNA obtained from mRNA of cancer cells (Bowes melanoma strain) [Goeddel, D. V., et al., UK Patent Application No. 8312221 (1983)], cDNA obtained from mRNA of normal cultured cells or genomic DNA clone obtained from human chromosome DNA [Ny, T., et al., Proc. Natl. Acad. Sci. U.S.A., 81, 5355 (1984)].

Some differences in DNA base sequences have already been recognized between the t-PA gene derived from cancer cells and the t-PA gene derived from normal cells [Ny, T., et al., Proc. Natl. Acad. Sci. U.S.A., 81, 5355 (1984)]. Under the present situation that the effects of the t-PA gene from cancer cells on carcinogenicity has not yet been proven, t-PA gene derived from normal cells must be used in the production of pharmaceutical products.

In order to express a desired foreign gene in animal cells, it is preferred to conduct transformation of the animal cells by using a vector in which the desired foreign gene is functionally coupled with regulatory DNA sequences. The term "regulatory DNA sequence" as used herein means sequences of promoters, termination and polyadenylation signals, enhancers and other expression-controlling sequences. One or more of these sequences can be employed as required. Effective sequences are chosen to give optimal expression in the specific animal cells employed as host cells. The stronger action of regulatory DNA sequences will give better results.

When host cells are Chinese hamster cells for instance, the SV40 (Simian Virus 40) DNA sequences may cause satisfactory results. The regulatory DNA sequences are however not limited to the above example but any regulatory DNA sequences may be employed equally so long as it can give high expression in Chinese hamster cells.

Regulatory DNA sequences to be employed in the present invention, which are expected to give high activity, may further include, for example, human metallothionein promoter [Karin, M., et al., Nature 308, 513 (1984)], mouse metallothionein promoter [Pavlakis, G. N. and Hamer, D. H., Proc. Natl. Acad. Sci. U.S.A., 80, 397 (1983)], mouse MuLV-LTR promoter (Anson, D. S., et al., Nature, 315, 683 (1985)], heat shock promoter [Peter Bromley and Richard Voellmy, European Patent Publication No. 118393-A2], adeno virus promoter [Wood, W. I., et al., Nature, 312, 330 (1984)], Human cytomegalovirus promoter [Boshart, M., et al., Cell, 41, 521 (1985)], etc.

Wild-type DHFR genes can be isolated from wild-type cells as a cDNA clone or a genome DNA clone. As wild-type DHFR genes, for example, mouse wild-type DHFR gene (Lee, F. et al., 1981, Nature, 294: 228), which is isolated in the form of cDNA clone and which is inserted in a vector, can be easily employed in the present invention.

In animal cells, folic acid is reduced by DHFR (dihydrofolate reductase) into tetrahydrofolic acid, an active form, and takes part in the synthesis of thymidylic acid. MTX, which is an analogue of folic acid, binds to DHFR and inhibits the activity of DHFR. Upon inhibition of the activity of DHFR by MTX, cells can no longer survive in a culture medium which does not contain any nucleic acid component.

In order to introduce a foreign wild-type DHFR gene into wild-type animal cells and to obtain a MTX resistant transformant in the presence of MTX surprisingly at such a high concentration that host cells cannot usually survive, it is necessary to get improved expression of the introduced DHFR gene in the wild-type cells.

For higher expression of the foreign DHFR gene, regulatory DNA sequences are artificially combined with a DHFR gene to form an expression vector. Where host cells are Chinese hamster cells for instance, the SV40 regulatory DNA sequences can result in a satisfactory expression. The effective regulatory DNA sequences are however not limited to those from SV40 but any regulatory DNA sequences which give higher DHFR expression in Chinese hamster cells may be employed.

Where a desired foreign gene and a wild-type DHFR gene are contained together on the identical expression vector, host cells are transformed by the vector. Where the desired foreign gene and the wild-type DHFR gene exist separately on separate expression vectors, host cells are transformed by a mixture of both expression vectors in suitable proportions.

By the term "animal cells" as used herein, any cells may be used so long as they are wild-type cells.

Characteristic properties desirable as host cells to used for industrial production, may be include cells that have cells have tolerance for any kind of stress and their culture is easy, their growth rate is fast, they permit high-density culture, their culture medium has a low serum demand, they have higher expression and secretion ability of foreign gene products potentially, they have the ability to glycosylate foreign gene products, and/or they produce much smaller amounts of endogenous substances related to the desired foreign gene products, etc.

When human t-PA gene is used as the desired foreign gene in particular and the t-PA gene is not derived from cancer cells, it is desirable to choose a continuous cell line as a host other than that derived from cancer cells because the desired products will not be accompanied with any contamination derived from cancer cells.

In the Example, cells satisfying the above-mentioned characteristic features to certain extents were discovered from among established Chinese hamster ovary cells (CHO) and lung cells (CHL) and those cells were used as a host. Needless to say, host cells shall not be limited to such illustrative examples.

As a method for introducing a vector DNA into host cells in the present invention, it is desirable to employ such a method that permits introduction of the vector DNA in a high yield because the screening of a transformant is undertaken under severe conditions in the subsequent stage. Good results can be obtained, for example, by introducing the vector DNA into the host in accordance with the modified calcium phosphate method including glycerin shock.

In order to apply a selection pressure to the DHFR gene as a dominant marker gene, a culture medium with MTX and free of nucleic acid components is used as a selective medium to screen a MTX resistant transformant. It is preferable to use, as a selective medium, a medium inhibiting the survival of host cells but permitting the survival of the transformant. Where the host cells are Chinese hamster cells for instance, it is desirable to use a selective medium containing MTX at a concentration of 0.1 $\mu$M–10 $\mu$M, preferably, 0.25 $\mu$M–1 $\mu$M.

The genetic amplification of the wild-type DHFR gene introduced in the transformant and the accompanying simultaneous amplification of the desired foreign gene may be carried out by a method known per se in the art. Reference for amplification of genes may be had, for example, to Schimke, R. T., in Gene Amplification, Edited by Schimke, R. T., Cold Spring Harbor Laboratory, P1, 1982. Regarding the simultaneous amplification of a DHFR gene and a desired gene in a transformant, reference may be had to Ringold, G., et al., J. Mol. Appln. Genet., 1, 165 (1981).

In the present invention, a strain having high productivity of a desired foreign gene product can be obtained by culturing a transformant resistant to MTX of a certain concentration in the medium containing MTX at a concentration 2–4 times higher than the first-mentioned MTX concentration to obtain cells rendered resistant to a much higher concentration of MTX and screening cells having a high production rate of the product of the desired foreign gene from the thus-obtained cells and then repeating the culturing and screening steps in the increasing concentration of MTX.

The principal characteristic feature of the present invention resides in the use of a wild-type DHFR gene instead of a mutant DHFR gene whose affinity with MTX is very low. This principal characteristic feature has brought about the following advantageous effects.

Namely, the genetic amplification can be performed at an MTX concentration (0.25 $\mu$M–50 $\mu$M, more preferably, 0.25 $\mu$M–20 $\mu$M) much lower compared with the MTX concentration (50 $\mu$M–1,000 $\mu$M) used in the genetic amplification when a mutant DHFR gene is employed. As a result, it is possible to obtain a stable transformant having a high productivity of the desired foreign gene product by use of such a lower concentration of MTX.

Owing to the use of an MTX concentration much lower than that conceivable in view of the prior art, the transformant of this invention shows good growth and its ability to produce the product of the desired foreign gene remains stable even after its long term cultivation.

The present invention will hereinafter be described more specifically by the following Example. It should however be borne in mind that this invention is not limited at all by the following Example.

EXAMPLE (1) Introduction of plasmid pSV-2 into Chinese hamster cells and expression of human t-PA gene:

Following the method described in U.S. patent application Ser. No. 932,209, a strain (MTC 017) having high t-PA producing ability was selected out of several normal human cells (chromosome number 2n=46) and was cultured on a large scale. Total RNAs were then extracted from the thus-cultured cells and poly(A)+mRNA was separated and recovered using oligo-dT cellulose.

Using the mRNA, a cDNA gene bank was prepared in accordance with the method proposed by Gubler and Hoffman [Gubler, U. and Hoffman, B. J., Gene, 25, 263 (1983)].

Employing a synthetic oligonucleotide probe reflecting the amino acid sequence of human t-PA, a cDNA encoding human t-PA gene was cloned. The entire base sequence of the t-PA gene was determined by the Maxam-Gilbert method [Maxam, A. M. and Gilbert, W., Proc. Natl. Acad. Sci., 74, 560 (1977)].

Plasmid pSV-2 to be expressed, the structure of which is shown in the accompanying drawing, was prepared by joining an enhancer, a replication-origin, promoter, and termination and andpolyadenylation signals, all derived from SV40, to each of the above-mentioned human t-PA cDNA sequences and mouse DHFR cDNA sequences [Lee, F., et al., Nature 294, 228 (1981)] and then integrating the thus-joined matter in a DNA fragment containing a bacterial replication origin and ampicillin-resistant marker derived from pML [Lusky, M. and Botchan, M., Nature, 293, 79 (1981)] in a manner employed in this field.

As host cells, Chinese hamster ovary cells (CHO) and lung cells (CHL) were used [Elkind, M. M. and Sutton, H., Radiation Research, 13, 556 (1960)].

The Chinese hamster ovary cells (CHO) or lung cells (CHL) were cultured at 37° C. in a Dulbecco's modified Eagle's medium (DME) supplemented with 5% fetal calf serum (FCS) in air containing 5% $CO_2$.

Cells were spread in a 60-mm dish at a rate of $5 \times 10^5$ cells per dish.

After culturing for 16 hours, pSV-2 DNA (5 µg or 10 µg per dish) was introduced into the cells by the calcium phosphate method [Graham, F. L. and Van der Eb., A. J., Virology, 52, 456 (1973)] following glycerol shock [Parker, B. A. and Stark, G. R., Virol, 31, 360 (1979)].

After culturing for further 48 hours, the cells were trypsinized and spread in several 35-mm dishes at a reduced cell density of one tenth the above-mentioned rate. They were cultured in DME-10% dialyzed FCS-0.25 µM MTX (a selective medium). The selective medium did not contain any nucleic acid components.

Three weeks later, 39 colonies appeared in total in two of the dishes in the experiment on the CHO cells. A similar experiment was conducted using a selective medium containing 0.5 µM MTX. The frequency of appearance of the MTX resistant transformant was reduced when compared with the result with 0.25 µM MTX.

Growth of the host cells in the selective medium containing 0.25 µm MTX was not detected when the plasmid pSV-2 was not introduced into the cells.

In the case of a selective medium containing 0.1 µM MTX, the host cells showed resistance and grew to confluence no matter whether the DNA of pSV-2 was introduced or not.

Sixteen colonies, which had been rendered resistant to 0.25 µM MTX, were separated using cloning rings, transferred to 12-well dishes, and then allowed to grow to confluent in a selective medium containing 0.25 µM MTX.

The culture medium was replaced by a fresh supply of the same culture medium and the cells were cultured for 24 hours. Fifteen milliliters of the culture supernatant were collected and the lytic activity of fibrin-clot was measured by the fibrin plate method [Rijken, D. C., et al., Biochim, Biophys. Acta, 580, 140 (1979)]. Twelve colonies showed activity (10–40 U/ml).

When anti t-PA serum was then mixed to the culture supernatant, the serum quenched the fibrin-clot lytic activity. The activity was however not lost even when anti-UK serum was mixed to the culture supernatant. It is hence clear that t-PA was contained in the culture supernatant.

After allowing the above-mentioned 12 clones to grow separately in 25-cm² flasks, they were spread at a low density ($10^2$–$10^3$ cells/dish) in 10-cm dishes. In a selective medium containing 0.25 µM MTX, the cells were cultured for about 2 weeks and 160 single clones were isolated.

(2) Measurement of t-PA activity:

The amount of t-PA produced by transformants was assayed by the following method.

The culture medium was removed from a 25-cm² flask with the grown cells adhered thereon and the inside of the flask was washed with phosphate-buffered saline. Thereafter, a small amount of 0.25% trypsin was added and the cells were separated from the bottom wall of the flask.

A suitable amount of a culture medium was then added to the flask and the cells were suspended thoroughly therein. The number of the cells was then counted, followed by dilution to prepare a cell suspension of $2 \times 10^5$ or $1 \times 10^5$ cells/ml. After placing 1 ml of the suspension in the wells of a 12-well dish and then maintaining the cells therein for 24 hours, 15 µl of the culture supernatant was used to measure the t-PA activity by the above-described fibrin plate method. No significant increase was observed to the number of cells after the 24-hour culture.

Since the fibrin plate method showed good reproducibility when the t-PA activity was measured around 50 U/ml, culture supernatants with higher activities were each measured after $\frac{1}{2}$–$\frac{1}{8}$ dilution.

(3) Genetic amplification by MTX:

In order to increase the production rate of t-PA by the t-PA producing transformant, genetic amplification was conducted in the following manner using the 160 single clones obtained in the above procedure (1) as a starting material.

The 0.25 µM MTX resistant transformant was spread at a density of $10^3$–$10^5$ cells/dish on a 10-cm dish and then cultured for about 2 weeks in a selective medium containing 1 µM MTX.

Colonies that appeared were isolated by using cloning rings and transferred to 24-well dishes, and were then allowed to grow to 90% confluent.

The culture medium was replaced by a fresh supply of the same culture medium and the cells were cultured for 24 hours. Thereafter, 15 µl of the culture supernatant was collected and its t-PA activity was measured by the fibrin plate method.

Cells of each clone, which showed high activity, were transferred to a 25-cm² flask and then cultured therein. The t-PA activity per unit cell number was measured by the activity measuring method described in the above procedure (2). In this manner, clones having higher t-PA producing ability were selected.

The cells of the thus-obtained high t-PA producing transformant were cultured in the presence of MTX of a much higher concentration. Out of cells rendered resistant to MTX of the much higher concentration, cells having higher t-PA producing rates were then screened. By successively repeating the above procedures, a high t-PA producing transformant was obtained. Some of the results are shown in the following table.

Incidentally, 0.25 µM MTX resistant transformants were also obtained similarly to CHO cells when CHL cells were used as a host. By genetic amplification with MTX, a high t-PA producing transformant was obtained from the 0.25 μM MTX resistant transformants of CHL.

TABLE

| Clone No. | MTX (μM) | t-PA production rate (U/ml/2 × 10$^5$cells) |
| --- | --- | --- |
| N75 | 0.25 | 34 |
| N104 | 0.25 | 27 |
| N135 | 0.25 | 32 |
| N104MIK6 | 1.0 | 50 |
| N104MIK17 | 1.0 | 61 |
| N135MIK8 | 1.0 | 46 |
| N104M2.5K3 | 2.5 | 134 |
| N104M2.5K14 | 2.5 | 122 |
| N135M2.5K6 | 2.5 | 138 |
| N135M2.5K29 | 2.5 | 124 |
| N104M5K8 | 5.0 | 344 |
| N104M5K21 | 5.0 | 340 |
| N135M5K3 | 5.0 | 384 |
| N135M5K9 | 5.0 | 324 |

After subjecting the resultant high t-PA production transformants to subculture for about 3 months using a selective medium, the activity was measured again. No deterioration to the t-PA producing ability was observed. The growth rate of the high t-PA producing transformants in the selective medium was 24–40 hours in terms of doubling time of the cells.

As has been described above, it is clear that an amplified transformant having high productivity of a foreign gene product can be obtained in accordance with the present invention, namely, by introducing a wild-type DHFR gene as a selective marker into wild-type animal cells to obtain a transformant thereof and then culturing the transformant in an amplification medium containing MTX at a concentration of 50 μM or lower as a DHFR inhibitor.

We claim:

1. A transformant obtained by the steps of:
   (a) introducing a vector into a wild type mammalian cell, said vector comprising Simian Virus 40 (SV40) regulatory DNA sequences, a heterologous wild-type DHRF cDNA gene and a structural gene encoding a heterologous gene product, in which the heterologous wild-type DHFR cDNA gene is linked to the SV40 regulatory DNA sequences controlling the expression of the heterologous wild-type DHFR cDNA gene;
   (b) culturing the wild-type mammalian cell, into which the vector is introduced, in a selective medium containing methotrexate at a concentration of 0.1 to 10 μM so as to select the transformant thus obtained; and
   (c) culturing the transformant thus selected in an amplification medium containing methotrexate at a concentration of 0.25 to 50 μM thereby amplifying both the heterologous wild-type DHFR cDNA gene and the structural gene.

2. The transformant of claim 1, wherein the heterologous wild-type DHFR cDNA gene is derived from a mouse cell line.

3. The transformant of claim 1, wherein the structural gene is a human t-PA gene.

4. The transformant of claim 3, wherein the human t-PA gene is derived from a normal cell.

5. The transformant of claim 4, wherein the human t-PA gene is derived from the MTC 017 strain.

6. The transformant of claim 5, wherein the human t-PA gene is cDNA, which is operably linked to SV40 regulatory DNA sequences controlling the expression of the human t-PA gene.

7. The transformant of claim 1, wherein the wild-type mammalian cells are wild-type Chinese hamster cells.

8. The transformant of claim 7, wherein the wild-type Chinese hamster cells are wild-type Chinese hamster ovary (CHO) cells.

9. The transformant of claim 7, wherein the wild-type Chinese hamster cells are wild-type Chinese hamster lung (CHL) cells.

10. A method of producing a transformant, which comprises the steps of:
    (a) introducing a vector into a wild type mammalian cell, said vector comprising Simian Virus 40 (SV40) regulatory DNA sequences, a heterologous wild-type DHFR cDNA gene and a structural gene encoding a heterologous gene product, in which the heterologous wild-type DHRF cDNA gene is linked to the SV40 regulatory DNA sequences controlling the expression of the heterologous wild-type DHFR cDNA gene;
    (b) culturing the wild-type mammalian cell, into which the vector is introduced, in a selective medium containing methotrexate at a concentration of 0.1 to 10 μM so as to select the transformant thus obtained; and
    (c) culturing the transformant thus selected in an amplification medium containing methotrexate at a concentration of 0.25 to 50 μM thereby amplifying both the heterologous wild-type DHFR cDNA gene and the structural gene.

11. The method of claim 10, wherein the heterologous wild-type DHFR cDNA gene is derived from a mouse cell line.

12. The method of claim 10, wherein the structural gene is a human t-PA gene.

13. The method of claim 12, wherein the human t-PA gene is derived from a normal cell.

14. The method of claim 13, wherein the human t-PA gene is derived from the MTC 017 strain.

15. The method of claim 14, wherein the human t-PA gene is cDNA, which is operably linked to SV40 regulatory DNA sequences controlling the express of the human t-PA gene.

16. The method of claim 10, wherein the wild-type mammalian cells are wild-type Chinese hamster cells.

17. The method of claim 16, wherein the wild-type Chinese hamster cells are wild-type Chinese hamster ovary (CHO) cells.

18. The method of claim 16, wherein the wild-type Chinese hamster cells are wild-type Chinese hamster lung (CHL) cells.

19. The method of claim 10 wherein the selective medium contains methotrexate at a concentration of 0.25 μM to 1 μM.

20. A method for producing a heterologous gene product which comprises culturing and amplifying the transformant of claim 1, and which further comprises the step of recovering the heterologous gene product.

* * * * *